(12) United States Patent
Arteta Montilva et al.

(10) Patent No.: US 12,315,160 B2
(45) Date of Patent: May 27, 2025

(54) METHOD AND APPARATUS TO PREDICT FEATURE STATE CHANGE WITHIN AN IMAGE

(71) Applicant: Optellum Limited, Oxford (GB)

(72) Inventors: Carlos Federico Arteta Montilva, Oxford (GB); Jerome Declerck, Oxford (GB)

(73) Assignee: Optellum Limited, Oxford (GB)

( * ) Notice: Subject to any disclaimer, the term of this patent is extended or adjusted under 35 U.S.C. 154(b) by 537 days.

(21) Appl. No.: 17/696,802

(22) Filed: Mar. 16, 2022

(65) Prior Publication Data

US 2023/0298177 A1 Sep. 21, 2023

(51) Int. Cl.
*G06T 7/00* (2017.01)
(52) U.S. Cl.
CPC .. *G06T 7/0014* (2013.01); *G06T 2207/10081* (2013.01); *G06T 2207/20081* (2013.01); *G06T 2207/20084* (2013.01); *G06T 2207/30064* (2013.01)

(58) Field of Classification Search
None
See application file for complete search history.

(56) References Cited

U.S. PATENT DOCUMENTS

| | | | | |
|---|---|---|---|---|
| 2014/0037170 A1* | 2/2014 | Sekiguchi | ............ | G06T 7/0012 382/131 |
| 2017/0216627 A1* | 8/2017 | Brooks | ................ | A61N 5/1048 |
| 2018/0053300 A1* | 2/2018 | Podilchuk | ............. | G06T 7/0016 |
| 2018/0220985 A1* | 8/2018 | Boroczky | ............. | G16H 50/20 |
| 2020/0211180 A1 | 7/2020 | Gillies | | |

(Continued)

FOREIGN PATENT DOCUMENTS

WO 2021146516 A1 7/2021

OTHER PUBLICATIONS

Tao Guangyu et al: "Prediction of future imagery of lung nodule as growth modeling with follow-up computed tomography scans using deep learning: a retrospective cohort study", Translational lung Cancer Research, vol. 11, No. 2, Feb. 1, 2022 (Feb. 1, 2022), pp. 250-262, XP093049717, Hong Kong ISSN: 2218-6751, DOI: 10.21037/tlcr-22-59 * p. 253-p. 256; figures 2, 5-7 *.

(Continued)

*Primary Examiner* — Leon Flores
(74) *Attorney, Agent, or Firm* — Optimus Patents US, LLC (57) ABSTRACT

A CADx system for analysing medical images to monitor at least one feature on the image to predict at least one of a change of the state or maintenance of the current state of a monitored feature within a time frame is described. The system comprising: an input circuit for receiving at least one medical input image; a feature state change circuit for analysing the received input image and predicting a state change comprising: a state change predictor to predict a state change of the monitored feature within the time frame; and an output circuit to output an indication of the change of state or maintenance of the current state of the monitored feature within the time frame based on the prediction of the feature state change predictor. A method of training a feature state change prediction circuit using Machine Learning is also described.

9 Claims, 8 Drawing Sheets

(56) References Cited

U.S. PATENT DOCUMENTS

2020/0320900 A1* 10/2020 Rossetto .............. G09B 23/286

OTHER PUBLICATIONS

Callister, M. E. J., et al. "British Thoracic Society guidelines for the investigation and management of pulmonary nodules: accredited by NICE." Thorax 70.Suppl 2 (2015): ii1-ii54.
MacMahon, Heber, et al. "Guidelines for management of incidental pulmonary nodules detected on CT images: from the Fleischner Society 2017." Radiology 284.1 (2017): 228-243.
Hiramatsu M, Inagaki T, Inagaki T, et al. Pulmonary ground-glass opacity (GGO) lesions-large size and a history of lung cancer are risk factors for growth. J Thorac Oncol. 2008;3:1245-50.
Chen D, Dai C, Kadeer X, et al. New horizons in surgical treatment of ground-glass nodules of the lung: experience and controversies. Ther Clin Risk Manag 2018;14:203-11. 10.2147/TCRM.S152127.
Qiu ZX, Cheng Y, Liu D, et al. Clinical, pathological, and radiological characteristics of solitary ground-glass opacity lung nodules on high-resolution computed tomography. Ther Clin Risk Manag 2016;12:1445-53. 10.2147/TCRM.S110363.
Pedersen JH, Saghir Z, Wille MM, Thomsen LH, Skov BG, Ashraf H. Ground-Glass Opacity Lung Nodules in the Era of Lung Cancer CT Screening: Radiology, Pathology, and Clinical Management. Oncology (Williston Park). Mar. 2016;30(3):266-74. PMID: 26984222.

* cited by examiner

METHOD AND APPARATUS TO PREDICT FEATURE STATE CHANGE WITHIN AN IMAGE

FIELD OF INVENTION

This invention relates to the field of Computer Aided Diagnosis (CADx) devices and methods for assisting the interpretation of medical images to support clinicians in healthcare. In particular, the field relates to risk Computer Aided Diagnosis devices to assist the reading and reporting of medical images by radiologists and the interpretation of the radiologist's report by the physician responsible for patient care.

BACKGROUND OF INVENTION

In the field of medical imaging, a variety of technologies can be used to investigate biological processes and anatomy. The following examples are types of scans that may be used to provide medical images: X-Ray; Computed Tomography (CT); Ultrasound (US); Magnetic Resonance Imaging (MRI); Single Photon Emission Tomography (SPECT); and Positron Emission Tomography (PET). Each type of scan is referred to as an "imaging modality".

Typically, a scan provides a "dataset". The dataset comprises digital information about the value of a variable at each of a plurality of spatial locations in either a two-dimensional or (more typically) a three-dimensional space. As a specific example, a CT scan may provide images of the chest of a patient. Such a CT scan might, as a more specific example, show features in the images, such as lung nodules in the chest.

Computer Aided Detection (CADe) devices serve to assist clinicians in assessing the medical images. CADe devices need to provide a clinician with standardised, objective, and repeatable information. The information typically relates to particular anatomical regions, including both normal tissue and lesions within a person. CADe devices may be used as a so-called 'Second Reader' device. Second Reader Devices are based on an approach whereby a radiologist first looks at an image resulting from a scan, for example a mammogram. The radiologist will then, based on training and experience, identify areas of the scan where the radiologist considers that there may need to be a further investigation, for example a biopsy. However, the radiologist can then consider the CADe findings. Those findings might involve a display to highlight any additional suspicious regions on the mammogram. The radiologist will then, based on training and experience, look at those further areas of the scan. The CADe device is thereby performing a second look at the scan. The results of the second look at the scan may be that the radiologist will be directed to areas of the scan that they had overlooked. In this way, CADe devices are designed to reduce 'false negatives', which are also termed 'missed findings'. Thus, CADe devices perform a support role to clinicians.

Computer Aided Diagnosis (CADx) devices are a related technology to CADe. CADx devices attempt to solve a different problem and relate generally to risk assessment. Instead of focusing on potentially missed findings as in CADe, they try to assist the user to classify findings correctly, for instance, either as malignant or benign in the case of potentially cancerous lesions. They rely on the user to identify abnormalities, and typically provide a score that is indicative of the risk of malignancy. Examples of commercial CADx devices are the breast cancer screening product 'Transpara™' from 'Screenpoint™', and the lung cancer product Virtual Nodule Clinic (VNC) from Optellum. There are many non-clinical CADx devices in the academic literature.

In the space of lung cancer, CADx devices have traditionally focused on evaluating features corresponding to lung nodules to produce malignancy risk scores, with the aim of helping clinicians make more appropriate decisions for the patient. A lung nodule is a small abnormal tissue in the lung (e.g., less than 30 mm in diameter) which is usually visible in X-ray based imaging modalities such as CT scans. Although the large majority of lung nodules are the result of benign conditions, they can also occur due to lung cancer, and hence they are always assessed for lung cancer risk. Examples of such lung cancer CADx devices include the Virtual Nodule Clinic (VNC) from Optellum, and qCT-Lung from qure.ai. The connection between risk assessment and clinical decision-making lies in that the most appropriate next step for a given patient with a lung nodule depends on the risk of it being malignant. For example, higher risk cases would warrant shorter term actions (e.g., PET/CT, biopsy, or short-term CT follow-up), while lower risk cases can be addressed with longer term CT follow-ups. The consensus of experts on how to link risk and clinical decision is collected in clinical guidelines published regularly by the relevant medical societies. In the case of lung cancer, these guidelines include those from the British Thoracic Society [1] and the Fleischner Society [2]. In these guidelines, risk assessment of the lung nodule is central to the decision-making process, hence it is thought that CADx devices that help clinicians better assess risk can lead to better management.

A common aspect among guidelines for the management of lung nodules is the existence of different management pathways according to the attenuation of the lung nodule. Nodule attenuation is a radiological description of the lung nodule feature as seen on CT images (or X-rays) and is a product of the X-ray absorption of the nodule as determined by its composition. In other imaging modalities, different compositions of the nodule tissue can also lead to visually different image patterns. There are two types of attenuations that are of common interest in the case of lung cancer diagnosis: solid and ground-glass opacity (GGO). These two attenuations can be present in a lung nodule either alone or together, forming three main classes of lung nodules of interest according to their attenuation: solid, pure ground-glass opacities (pGGO), and part-solid or mixed. Examples of these nodule classes can be seen in FIG. 2. Historically, guidelines for solid and part-solid nodules have been more precise as those types of lung nodules have been better characterized and appear to have a more predictable behaviour. On the other hand, there is more uncertainty around the progression of pGGO nodules, thus their optimal management remains an open question. For example, if a solid nodule appears stable in size over a period of 2 years, it is safe to consider it benign, and potentially not follow it up any longer. On the other hand, pGGO nodules can still grow significantly after 2 years of stability [3]. Therefore, clinical guidelines recommend much longer observation periods for pGGO nodules than solid or semi-solids.

A crucial aspect of pGGO nodules is that, even when caused by malignant disease, these would not typically be aggressive lesions. Instead, they would likely correspond to pre-invasive types such as adenocarcinoma in situ (AIS) and atypical adenomatous hyperplasia (AAH), or to minimally-invasive adenocarcinoma (MIA) [4, 5, 6]. It is therefore unclear whether there is an immediate need to resect or treat them, and long-term follow-ups are acceptable. However, in some cases, pGGO nodules undergo a change of state known as a solid transformation, where a solid component appears, thus turning the pGGO nodule into part-solid. It is thought that the solid component of part-solid nodules caused by malignant disease represent tissue invasion [6], and it is then critical to speed up the diagnosis and treatment.

State-of-the-art CADx devices for lung cancer, even if they are approved for use on pGGO nodules, will only inform on the risk that the nodule was caused by malignant disease. Therefore, they provide no indication of the urgency with which the patient should be definitively diagnosed, for example, with invasive procedures.

When a CADx device operates on features corresponding to lung nodules, this invention addresses the special needs of lung cancer diagnosis CADx devices for pGGO nodules by extending the capabilities beyond the standard malignancy risk score. Specifically, it adds the capability of predicting when potentially malignant pGGO nodules will undergo solid transformation, thus providing clinicians with key information for their decision making.

REFERENCES

[1] Callister, M. E. J., et al. "British Thoracic Society guidelines for the investigation and management of pulmonary nodules: accredited by NICE." *Thorax* 70. Suppl 2 (2015): ii1-ii54.
[2] MacMahon, Heber, et al. "Guidelines for management of incidental pulmonary nodules detected on CT images: from the Fleischner Society 2017." *Radiology* 284.1 (2017): 228-243.
[3] Hiramatsu M, Inagaki T, Inagaki T, et al. Pulmonary ground-glass opacity (GGO) lesions-large size and a history of lung cancer are risk factors for growth. J Thorac Oncol. 2008; 3:1245-50.
[4] Chen D, Dai C, Kadeer X, et al. New horizons in surgical treatment of ground-glass nodules of the lung: experience and controversies. Ther Clin Risk Manag 2018; 14:203-11. 10.2147/TCRM.S152127
[5] Qiu Z X, Cheng Y, Liu D, et al. Clinical, pathological, and radiological characteristics of solitary ground-glass opacity lung nodules on high-resolution computed tomography. Ther Clin Risk Manag 2016; 12:1445-53.10.2147/TCRM.S110363
[6] Pedersen J H, Saghir Z, Wille M M, Thomsen L H, Skov B G, Ashraf H. Ground-Glass Opacity Lung Nodules in the Era of Lung Cancer CT Screening: Radiology, Pathology, and Clinical Management. Oncology (Williston Park). 2016 March; 30(3):266-74. PMID: 26984222.

SUMMARY OF THE INVENTION

Accordingly, the invention seeks to mitigate, alleviate, or eliminate one or more of the abovementioned disadvantages singly or in any combination.

According to the invention there is provided a CADx system for analysing medical images to monitor at least one feature on the image to predict at least one of a change of the state or maintenance of the current state of a monitored feature within a time frame comprising: an input circuit for receiving at least one medical input image; a feature state change circuit for analysing the received input image and predicting a state change comprising: a state change predictor to predict a state change of the monitored feature within the time frame; and an output circuit to output an indication of the change of state or maintenance of the current state of the monitored feature within the time frame based on the prediction of the feature state change predictor.

Preferably, the feature state change circuit further comprises a feature attenuation classifier that activates the feature state change circuit when the at least one monitored state in a feature is detected.

In an embodiment of the invention, the output circuit also provides an output of the current state of the monitored feature.

Preferably, the feature state change circuit also predicts the resolution of the monitored feature.

Further preferably, the medical image is an image showing at least part of a lung.

In an embodiment of the invention, the monitored feature is a lung nodule and the change of state of the monitored feature is from a pure ground glass opacity nodule to a solid or part solid nodule.

Preferably, the output circuit further outputs a disease risk score for the input medical image.

Further preferably, the input further comprises one or more biomarkers or clinical parameters for the patient. In an embodiment of the invention, the clinical parameters and biomarkers comprise at least one of: patient age, patient sex, results of blood tests, results of lung function tests.

Preferably, the input medical image is one of: X-ray image, CT image, ultrasound image, MRI image, SPECT image or a PET image.

According to the invention, there is also provided, a method of training a feature state change prediction circuit using a Machine Learning model to predict the change of state of different features on medical images comprising the steps of providing a training dataset of input images with temporal information about the change of state in the features in each image in the dataset; providing at least one image from the training set to the feature state change prediction circuit to produce a time prediction for when a feature in the image will change state; comparing the time prediction with the original temporal information for the image and calculating an error in the feature state change prediction based on the comparison; updating one or more parameters for the feature state change prediction circuit following the calculation of the error to minimise the calculated error; repeating the above steps until a pre-set convergence level between the prediction and the ground truth level is reached.

Preferably, the training dataset is a set of lung images. Further preferably, the features on the lung image are lung nodules. Preferably, the images in the training dataset are CT images.

In an embodiment of the invention, the machine learning model is a classification model or a regression model. Further preferably, the machine learning model is based on a neural network.

In an embodiment of the invention, the temporal information in the training images preferably indicates whether a feature changed state within a pre-determined length of time. In an embodiment of the invention, the temporal information indicates if a lung nodule in the image transformed from a pure ground glass opacity nodule to a solid or part solid nodule before a pre-determined length of time.

In an embodiment of the invention, the temporal information in the training images preferably indicates whether the state of a feature remained unchanged within a pre-determined length of time. In an embodiment of the invention the temporal information in the training images indicate whether a pure ground glass opacity nodule remained untransformed for at least a pre-determined length of time.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION

Overview of the Invention

This invention consists of CADx system for analysing medical images to monitor at least one feature on the input image to predict a time frame for at least one of a change of the state or maintenance of the current state of a monitored feature.

In a preferred embodiment, where the monitored feature corresponds to pure Ground Glass Opacity (pGGO) lung nodules, and the change of state corresponds to a transformation from pGGO to semi-solid or solid, this invention extends existing CADx devices for lung cancer diagnosis by providing information that is specific for the clinical management of pGGO nodules. Specifically, pGGO nodules tend to become concerning only at the point at which they develop a solid component, a process known as solid transformation, after which they become semi-solid or solid. Given the high variability with which this can happen, the management of pGGO nodules consists of long follow-up processes, e.g., every year for 5 years or more. Therefore, an estimate of when the solid transformation of the nodule would occur could allow for more personalized clinical management decisions, potentially reducing the time for diagnosis of those pGGO nodules which are estimated to convert prior to the recommended follow-up time. A device where this invention is implemented is thus referred to as a CADx device with feature state change.

Figure 1:
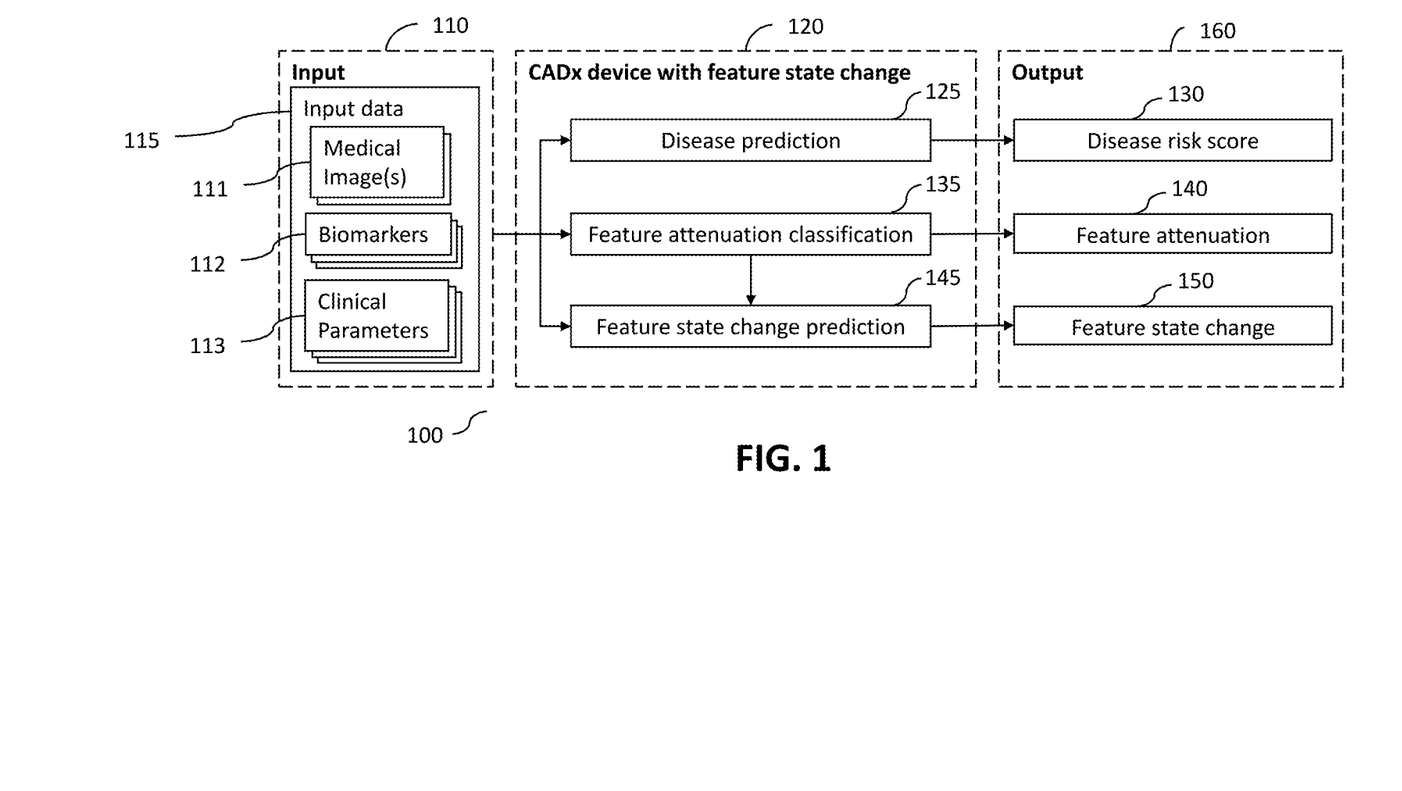
FIG. 1 illustrates a CADx system according to an embodiment of the invention.

The CADx device with feature state change is illustrated in FIG. 1. Like standard CADx devices, the CADx device with feature state change has an input circuit 110 which supplies the input data 115 for analysis by the CADx device 120. A unit of input data 115 contains a least one medical image 111, showing different features on the image, where the features are to be monitored. Preferably the image is either an X-ray image, CT image, ultrasound image, MRI image, SPECT image or a PET image. Preferably, the image will be an image showing at least part of a lung, and the feature on the image will be a lung nodule. Preferably, the monitored feature is a pGGO lung nodule and the change of state of the monitored feature is from a nodule with pure ground glass opacity to a solid or part sold nodule.

Preferably, an embodiment of the invention provides a CADx device for analysing medical images to monitor at least one feature on the image to predict a time frame for at least one of a change of the state or maintenance of the current state of a monitored feature comprising: an input circuit for receiving at least one medical input image: a feature state change circuit for analysing the received input image and predicting the time for state change comprising: a feature state change predictor to predict a time for a state change of the monitored feature; and an output circuit to output an indication of the time period for the change of state or maintenance of the current state of the monitored feature based on the prediction of the transformation predictor.

In an embodiment of the invention, the input image may be provided in combination with one or more clinical parameter 112 such as patient age and sex, and the result of relevant tests such as biomarkers 113, e.g., a test for a gene mutation associated with an increased risk of cancer. Other examples of clinical parameters are results of blood tests, lung function tests, patient or family history of disease, body weight, and location of a suspicious lesion. Once the input data 115 is presented to the input circuit 110 of the CADx device 120, the input data is processed by a disease prediction circuit 125, typically based on a machine learning model that is trained to predict a risk score of a disease given the input data. Preferably the disease risk score is a score for the risk of lung disease. For example, the machine learning model can consist of a classification or a regression model. Regardless of the specific machine learning model, the disease prediction circuit 125 performs a series of mathematical operations on the values of the input data resulting in a disease risk score 130 that is provided via the output circuit 160. The disease risk score is typically a number indicative of the likelihood that the unit of input data 115 corresponds to that of a malignant case. For instance, if the input data consist of a CT image of a lung nodule, as it would be typically the case in CADx devices for lung cancer diagnosis, then the risk score is indicative of the likelihood that the lung nodule is malignant.

Unlike standard CADx devices, the CADx device with feature state change has a feature state change prediction circuit 145 which is activated when the feature in the image being presented in the input data corresponds to a monitored feature such as pGGO nodules. Preferably, the activation of the transformation prediction circuit is decided by a feature attenuation classification circuit 135, which determines the attenuation of the feature, preferably the attenuation of the feature in the input data, for instance, is the nodule attenuation solid, part-solid, or pGGO. Once the feature state change prediction circuit 145 has been activated, it processes the input data 115 with a series of mathematical operations resulting in an output 150 which is indicative of when the monitored feature, preferably the pGGO nodule in the input data, is expected to change state; preferably, go through transformation. The various circuits which differentiate the CADx device with feature state change from current CADx devices are described next. In an embodiment of the invention, the output circuit may also output an indication of the time period for the change of state or maintenance of the current state of the monitored feature based on the prediction of the feature state change prediction circuit 145.

Feature Attenuation Classification Circuit

Figure 2:
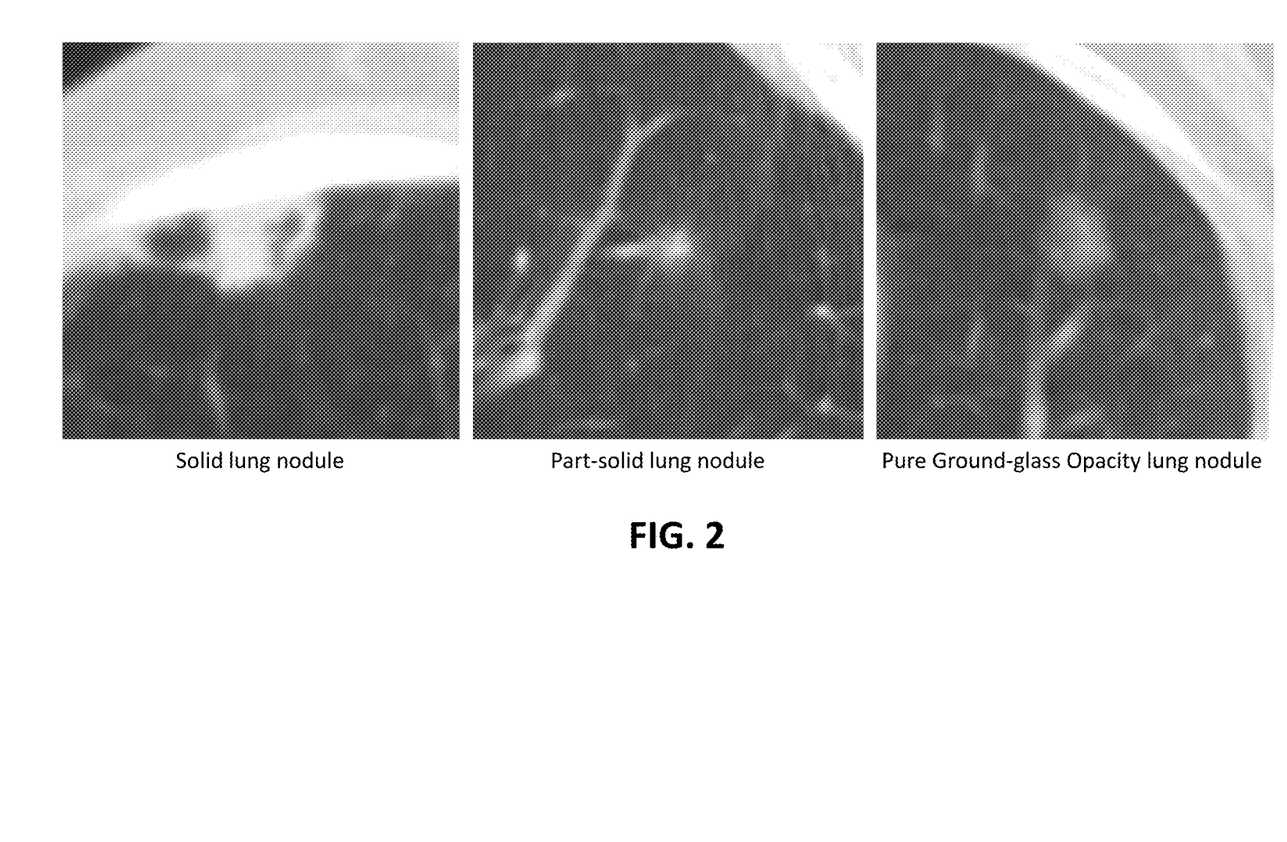
FIG. 2 shows examples of different types of lung nodules according to their attenuation.

The feature attenuation classification circuit 135 is responsible for determining the attenuation of a feature that is present on the input data, for instance, if the feature is a lung nodule, the classification circuit will determine if the nodule as shown in the input image is solid, part-solid, or pGGO, as shown in FIG. 2. Preferably the feature attenuation classifier is a feature attenuation classification circuit 135 that takes as input a unit of input data 115. The input data 115 typically contains at least one CT image of the a feature, preferably a lung nodule, for which the attenuation needs to be determined, and applies a series of mathematical operations which results in an output that is indicative of the attenuation of the lung nodule in the unit of input data 115.

Figure 3:
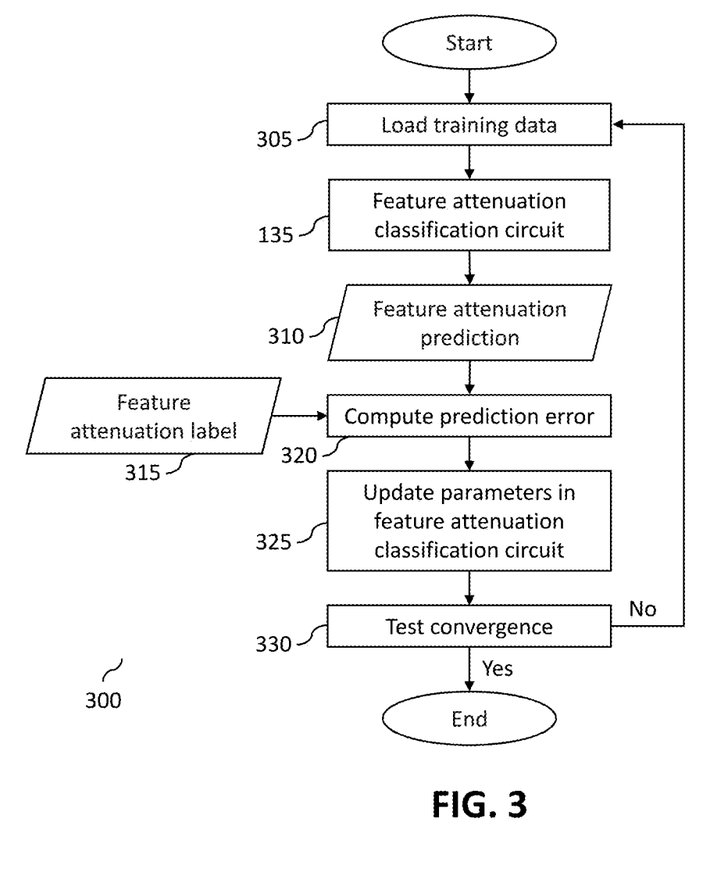
FIG. 3 shows an embodiment of a training process for feature classification according to its attenuation.

In some implementations of this invention, the feature attenuation classification circuit 135 is based on a machine learning model, for instance, a classification model or a regression model. In such an implementation, the feature attenuation classification circuit 135 is obtained through a process of model training, for instance, as shown in FIG. 3. Aside from the model being trained 135, the training process requires two additional elements: a corpus of training data with the same elements as the input data 115 to the CADx device, and the associated ground truth attenuation labels for each element of the training data. For example, the training data can consist of CT images containing features, such as lung nodules of a variety of attenuations, and each image would have an associated ground truth label indicating the attenuation of the lung nodule (pGGO, semi-solid or solid) in it as determined by an expert (e.g., a radiologists).

The training process 300 is preferably an iterative process. Each iteration of the training process starts by loading the corpus of training data 305, either completely or partially, but at least one training sample and ground truth label, and providing the training data to the feature attenuation classification circuit 135. For each sample in the loaded training data, the feature attenuation classification circuit 135 produces a prediction 310 of the feature attenuation in the image. Preferably, this is a determination of the current attenuation of the feature in the image. So, for example, the features will be classified as pGGO, semi-solid or solid in the case of lung nodules. This prediction of the feature attenuation is then compared with a feature attenuation ground truth label 315 in order to produce a prediction error 320, which is a measure of mismatch between the attenuation prediction and the attenuation ground truth label, for each sample in the training data.

The prediction error 320 is then used to update the parameters of the attenuation classification circuit 135 in such a way that minimizes the prediction errors previously computed 320. An iteration finalizes with a test for convergence 330, which evaluates whether a stopping criterion has been reached. In some examples, the test for convergence consists of evaluating a metric such as prediction error on a subset of the training data, typically one that is not used to compute the prediction errors 320 that lead to updating the parameters of the feature attenuation classification circuit 325; if this metric fulfils a criterion such as not having changed since the las iteration of the process 300, then the training process ends. Otherwise, another iteration starts, and the iterations are repeated until the test for convergence is satisfied.

Once the training process 300 has converged, the feature attenuation prediction circuit 135 can predict the feature attenuation (pGGO, semi-solid or solid in the preferred case of lung nodules) on new data units 115 that are input into the deployed CADx device.

In some example implementations of the feature attenuation circuit 135, the feature attenuation circuit is based on a deep neural network. In some examples, the deep neural network implements a classification model. Typically, the raw output of the classification deep neural network for a given unit of input data 115 consists of scalar values $s_k$, where k is the index of the attenuation type among K types of feature classes according to their attenuation. In some example implementations, the scalar values $s_k$ are transformed into a probability distribution using a softmax function $$p_k = e^{s_k} / \Sigma_{k=1}^{K} e^{s_k} \quad (1)$$

where $p_k$ is now the estimated probability that the feature in the input data was of attenuation type k. In some example implementations, a decision on the specific type of attenuation (the feature classification) out of all the possible attenuation types is determined as $$\text{FeatureAttenuation} = \text{argmax}_{k \in K}(p_k) \quad (2)$$

In other examples of this invention, the feature attenuation circuit 135 is equivalently based on different classification models such as support vector machines or random forests.

In some examples of this invention, the output of the feature attenuation circuit 135, for instance the predicted feature attenuation 140 as in EQ. 2, is used as an input to the feature state change prediction circuit 140 to control its activation, as described in the details of the feature state change prediction circuit, and hence produce a feature state change prediction 150, preferably a prediction of when a pGGO nodule will change stage (e.g., transform to semi-solid or solid).

In some examples of this invention, the predicted feature attenuation from EQ. 2 is given to the output circuit 160 of the CADx device such that it can be presented to the user as the feature attenuation output 140. This may be presented visually on a display, or as an audio output for example. Since the predicted feature attenuation may drive the activation of the feature state change prediction circuit 145, showing the predicted feature attenuation 140 to the user can be useful to understand why a feature state change output is not given for a particular input (e.g., the CADx device did not interpret the input data unit 115 to contain a pGGO nodule). In an embodiment of the invention, the output circuit may also provide an output of the current state of the monitored feature, for instance whether a lung nodule is pGGO, semi-solid or solid. Preferably the output circuit 160 may provide one or more of a disease risk score 130, the current state of a monitored feature (in the case of a lung nodule this will be the current nodule attenuation), and a feature state change prediction, to predict a time period for a change of state or the maintenance of the current state of a monitored feature, that is when a feature will undergo a change of state.

Feature State Change Prediction Circuit

The feature state change prediction circuit 145, is responsible for producing a number that can indicate to the user of the CADx device when a feature in the input will undergo a change of state, that is to provide an indication of the time for a change of state to occur. In a preferred embodiment of the invention this is when a pGGO nodule in the input data is predicted to go through solid transformation. Having an indication of when the pGGO nodule may transform to semi-solid or solid (i.e., develop a solid component) can help the clinical decision making such as choosing the best interval for a follow-up study.

Like the feature attenuation classification circuit 135, or the disease prediction circuit 125, the feature state change prediction circuit 145 is typically based on a machine learning model. For example, a classification model or a regression model. Nevertheless, the process of training the feature state change prediction circuit 145 will differ from that of the attenuation prediction circuit (e.g., FIG. 3) in an important way: in practice, the ground truth labels for when the change of state of the features, preferably the transformation of the pGGO nodules, occurs, cannot be obtained from domain experts. The reason is that, typically, pGGO nodules are monitored on a regular but infrequent basis (typically annually or longer) as indicated by clinical guidelines, thus once a pGGO has transformed to semi-solid or solid, it is not possible to know at which point between the available medical images this transformation of the pGGO nodule would have occurred. Therefore, several different embodiments of the feature state change prediction circuit 145 are described in this invention. All these different embodiments circumvent the lack of ground truth labels for when the state change of the monitored feature, in this case the transformation of the pGGO nodule, occurred. This is done in different ways for different embodiments, while still providing the user with useful related information that aids clinical management of lung nodules.

Embodiment 1—Changed State by Next Follow-Up

In this embodiment of the invention, the feature state change prediction circuit 145 predicts whether a feature, preferably a pGGO nodule, in the input data 115 will have changed state, preferably transformed to solid or semi-solid, within a pre-determined length of time. This will generally be the time the next standard follow-up is due, denoted $t_{fu}$. For instance, a year later (i.e., $t_{fu}$=1 year for pGGO nodules), which is currently the recommended follow-up time for pGGO nodules of at least 6 mm in size in the British Thoracic Society guidelines [1]. If the CADx device for lung cancer predicts that a pGGO nodule is likely to have transformed by the next standard follow-up time $t_{fu}$, then the managing clinician could decide to shorten the follow-up time for this patient.

This invention also provides a method of training a feature state change prediction circuit using a Machine Learning model to predict the change of state of different features on medical images comprising the steps of providing a training dataset of input images with temporal information about the change of state in the features in each image in the dataset; providing at least one image from the training set to the state change prediction circuit to produce a time prediction for when a feature in the image will change states; comparing the time prediction with the original temporal information for the image and calculating an error in the state change prediction based on the comparison; updating one or more parameters for the state change prediction circuit following the calculation of the error to minimise the calculated error; repeating the above steps until a pre-set convergence level between the prediction and the ground truth level is reached.

Figure 5:
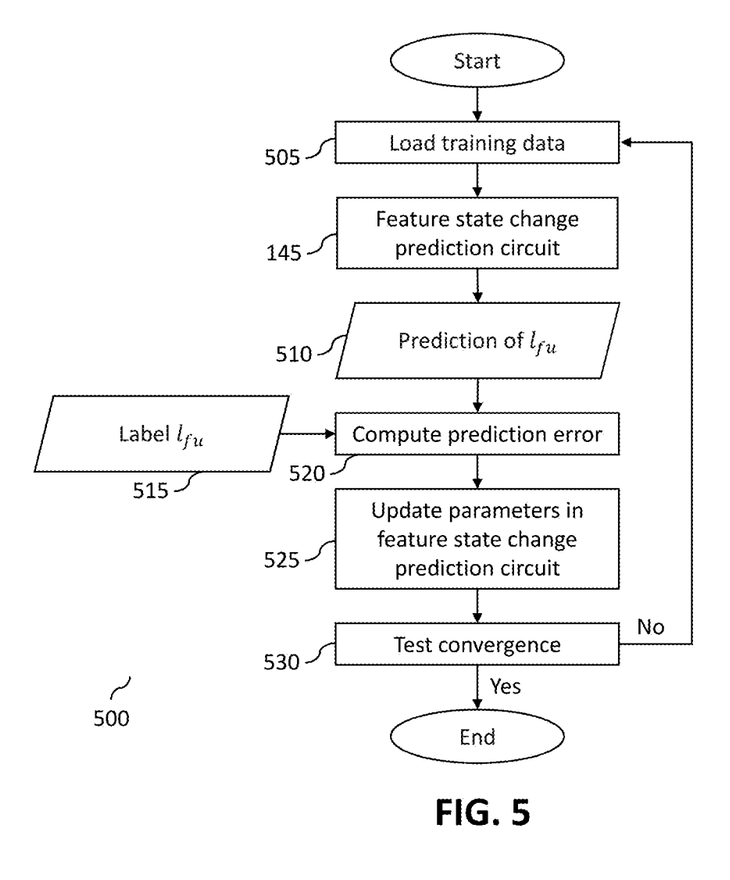
FIG. 5 shows a method a training a machine learning model according to a first embodiment of the invention.

In an embodiment of the invention, training of the feature state change prediction circuit 145 can be done following the process 500 shown in FIG. 5. The training process 500 requires a corpus of training data, as would be input to the CADx device 115 (e.g., CT images showing all or part of a lung, where the images may also show features such as lung nodules), made up of features, preferably, pGGO nodules for which it can be determined whether the nodule had transformed by $t_{fu}$. For instance, follow-up studies exist for these pGGO nodules. The output of this determination is denoted as the changed-state-by-$t_{fu}$ label, $l_{fu}$. For example, if the training data was collected from sites which comply with a $t_{fu}$ follow-up schedule for pGGOs, then an expert (e.g., radiologist) can determine the label $l_{fu}$ for any pGGO by assessing whether the pGGO nodule transformed in the follow-up study. In pGGO cases where the follow-up images were not collected at $t_{fu}$ time, $l_{fu}$ can often be deduced by the expert. For example, if pGGO nodules were followed in a time less than $t_{fu}$, those which transformed can be included in the training data as it follows that they had transformed by $t_{fu}$ as well. Likewise, if pGGO nodules were followed in a time greater than $t_{fu}$, those which did not transformed can be included in the training data as it follows that they had not transformed by $t_{fu}$.

Once the training data and associated labels $l_{fu}$ are available, this embodiment of the feature state change prediction circuit 145 can be trained following 500. The training process 500 is preferably an iterative process. Each iteration starts by loading the corpus of training data 505, either completely or partially, and giving it to the feature state change prediction circuit 145. For each sample in the loaded training data, the feature state change prediction circuit 145 produces a prediction 510 of whether the feature will have transformed by the time $t_{fu}$, denoted as $\hat{l}_{fu}$. This prediction $\hat{l}_{fu}$ is then compared with the label $l_{fu}$ 515 to produce a prediction error 520, a measure of mismatch between the prediction $l_{fu}$ and the label $l_{fu}$. The prediction error 520 is then used to update the parameters of the feature state change prediction circuit 145 in such a way that minimizes the prediction errors previously computed 520. An iteration finalizes with a test for convergence 530, which evaluates whether a stopping criterion has been reached. In some examples, the test for convergence consists of evaluating a metric such as prediction error on a subset of the training data, typically one that is not used to compute the prediction errors 520 that lead to updating the parameters of the feature state change prediction circuit 525; if this metric fulfils a criterion such as not having changed since the las iteration of the process 500, then the training process ends. Otherwise, another iteration starts.

Once the training process 500 has converged, the feature state change prediction circuit 145 can predict, for data units 115 with the monitored features, whether they would change state by time $t_{fu}$.

In some example implementations of the feature state change prediction circuit 145, its structure is based on a deep neural network. In some examples, this deep neural network implements a classification model with two possible classes $c \in [0, 1]$ denoting whether the monitored feature, preferably a monitored lung nodule, and more preferably, a pGGO lung nodule, changes states by $t_{fu}$ or not. Typically, the raw output of the two-class classification deep neural network for a given unit of input data 115 consists of a scalar value se for each of the two possible classes. In some example implementations, the scalar values $s_c$ are transformed into a probability distribution using a softmax function $$p_c = e^{s_c} / \Sigma_{c=1}^{C} e^{s_c} \quad (3)$$

Given that there are only two outcomes on this probability distribution, $p_c$ can be summarized with a single value $p_{t_{fu}}$ which is indicative of the probability that the monitored feature, preferably the pGGO nodule in the input data 115 will have transformed by $t_{fu}$.

In some examples of this invention, the value $p_{t_{fu}}$ is given to the output circuit 160 of the CADx device and presented to the user as the feature state change 150, preferably this is the transformation of the pGGO lung nodule. In other examples of this invention, the value $p_{t_{fu}}$ is converted into a binary indicator of feature state change by thresholding it in the following way $$ChangedStateByFollowUp = \begin{cases} \text{Yes, if } p_{t_{fu}} \geq T_{th} \\ \text{No, if } p_{t_{fu}} < T_{th} \end{cases} \quad (4)$$

Here, $T_{th}$ is a state change threshold which is empirically set according to the clinical use-case of the CADx device. That is, it is a pre-determined time threshold. For instance, in the preferred case of monitoring pGGO nodules, a low $T_{th}$ would mean that the pGGO nodule transformation may be detected with high sensitivity but low specificity (e.g., a rule-out test), while a high $T_{th}$ would mean that the pGGO nodule transformation may be detected with lower sensitivity but high specificity (e.g., a rule-in test). Some other use cases may benefit from choice of $T_{th}$ which balances sensitivity and specificity. All these scenarios can have different clinical use-cases, thus can be chosen depending on the requirements a specific deployment of the CADx device with feature state change.

Embodiment 2—Time with No State Change

In this alternative embodiment of the invention, the feature state change prediction circuit 145 predicts the time a monitored feature, preferably a pGGO nodule, in the input data 115 is expected to remain in its current state (e.g., in a pGGO state in the case of a pGGO nodule), denoted $t_u$. For instance, the lung cancer CADx device may predict a pGGO nodule will remain untransformed for a period considerably larger than the standard follow-up time for pGGO nodules, prompting the managing clinician to increase the follow-up period for this patient.

Figure 6:
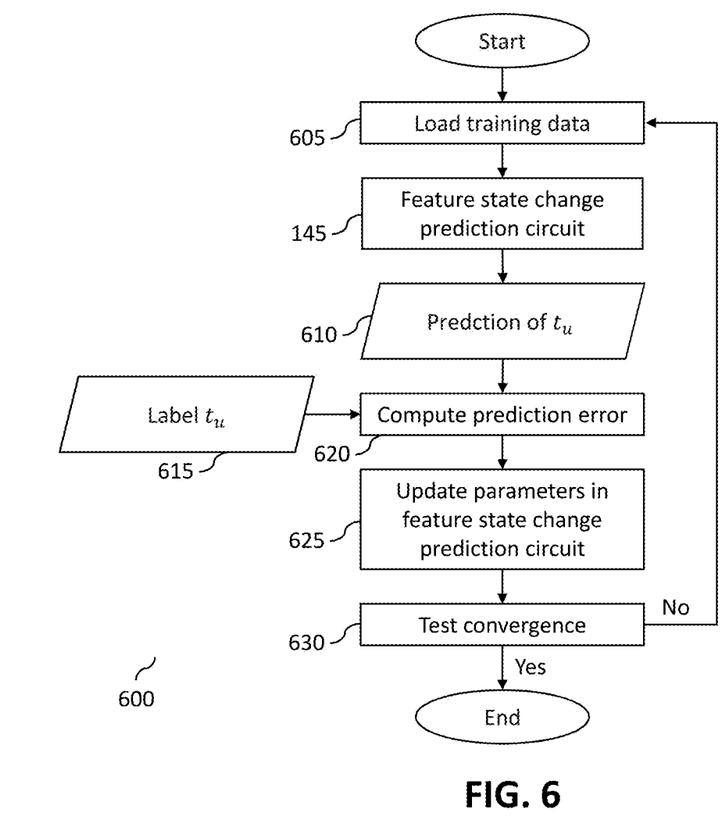
FIG. 6 shows a method a training a machine learning model according to a second embodiment of the invention.

In a further embodiment of the invention, training of the feature state change prediction circuit 145 can be done following the process 600 shown in FIG. 6. The training process 600 requires a corpus of training data, as would be input to the CADx device 115 (e.g., CT images), showing features that are to be monitored. Preferably, the training data is made up of CT images showing all or part of a lung, preferably the images also show features to be monitored, such as lung nodules. In a preferred example of this embodiment of the invention, the training images show pGGO nodules for which it can be determined the time $t_u$ that the nodules remained untransformed. For instance, if follow-up studies exist for these pGGO nodules, an expert (e.g., radiologist) can determine $t_u$ for a subset of the cases. For example, a pGGO nodule which was imaged 3 times, with one year between imaging studies, and remaining untransformed throughout (so it remained in the pGGO state, and did not become solid or semi-solid) could contribute the first and second image to the corpus of training data, with labels $t_u=2$ years and $t_u=1$ year respectively.

Once the training data and associated labels to are available, this embodiment of the feature state change prediction circuit 145 can be trained following 600. The training process 600 is preferably an iterative process. Each iteration starts by loading the corpus of training data 605, either completely or partially, and giving it to the feature state change prediction circuit 145. Preferably the training data is a set of images, such as CT images. For each sample in the loaded training data, the feature state change prediction circuit 145 produces a prediction 610 of the time the feature in the training image will remain in its current state. Preferably, the feature is a pGGO nodule that will remain untransformed; this prediction is denoted as $\hat{t}_u$. The prediction $\hat{t}_{f_u}$ is then compared with the label $t_u$ 615 to produce a prediction error 620, a measure of mismatch between the prediction $\hat{t}_u$ and the label $t_u$. The prediction error 620 is then used to update the parameters of the feature state change prediction circuit 145 in such a way that minimizes the prediction errors previously computed 620.

An iteration finalizes with a test for convergence 630, which evaluates whether a stopping criterion has been reached. In some examples, the test for convergence consists of evaluating a metric such as prediction error on a subset of the training data, typically one that is not used to compute the prediction errors 620 that lead to updating the parameters of feature state change prediction circuit 625; if this metric fulfils a criterion such as not having changed since the las iteration of the process 600, then the training process ends. Otherwise, another iteration starts.

Once the training process 600 has converged, the feature state change prediction circuit 145 can predict, for data units 115 with the monitored features, the time that the feature in the image will remain unchanged. Preferably, the feature is a pGGO nodule, and the predicted time is the time the pGGO nodules are expected to remain untransformed.

In some example implementations of the feature state change prediction circuit 145, its structure is based on a deep neural network. In some examples, this deep neural network implements a regression model, thus regressing the value $t_u$. Typically, the raw output of the regression deep neural network for a given unit of input data 115 consists directly of the scalar value $\hat{t}_u$.

In some examples of this invention, the value $\hat{t}_u$ is given $\hat{t}_u$ the output circuit 160 of the CADx device and presented to the user as the feature state change information 150.

Activation of the Feature State Change Prediction Circuit

Figure 4:
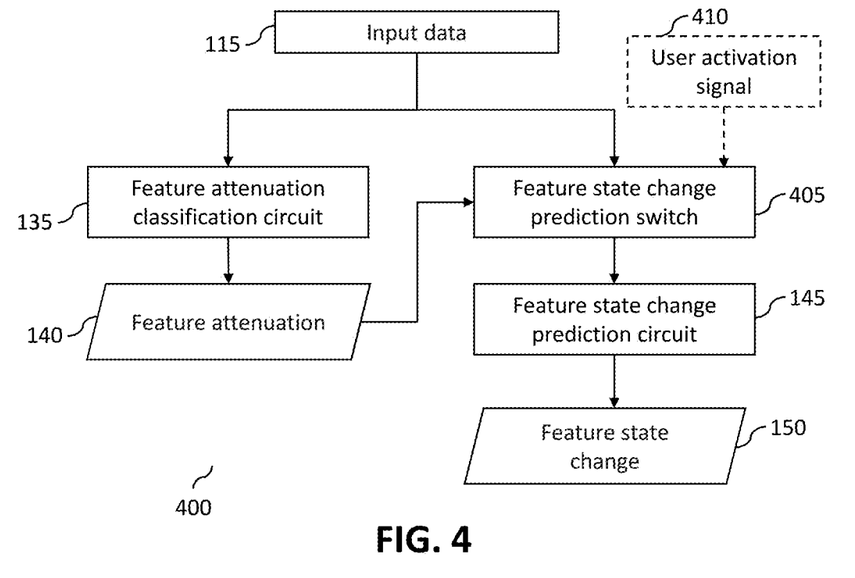
FIG. 4 shows an arrangement of a CADx device with a feature state change circuit.

In an embodiment of the invention the prediction task performed by the feature state change prediction circuit 145 is applicable to monitored features, preferably pGGO nodules. Nevertheless, the CADx device may be used for other features. For instance, a CADx device for lung cancer diagnosis may also be used on nodules with any type of attenuation, such as solid, semi-solid, and not only pGGO. Therefore, some examples of this invention may automatically activate the feature state change prediction circuit 145 when the presence of a monitored feature is detected in the unit of input data 115; preferably a pGGO nodule. For instance, as shown in FIG. 4, an implementation of this invention contains a feature state change prediction switch 405 which controls the activation of the feature state change prediction circuit 145. In some examples of this invention, the feature state change prediction switch 405 takes as input the feature attenuation prediction (EQ. 2) and activates the feature state change prediction circuit 145 only if the monitored feature is detected. Likewise, the feature state change prediction circuit 145 will not be activated for a unit of input data 115 that is not predicted to contain a specific monitored feature, preferably a pGGO nodule.

In some examples of this invention, the activation mechanism implemented in the switch 405 can be overwritten by a user activation signal 410, also shown in FIG. 4. For example, if the feature attenuation classification circuit 135 fails to detect the presence of a monitored feature such as a pGGO nodule in the unit of input data 115 which the user does detect, the user can still prompt the system to produce a feature state change 150.

Feature Resolution Prediction Circuit

Figure 7:
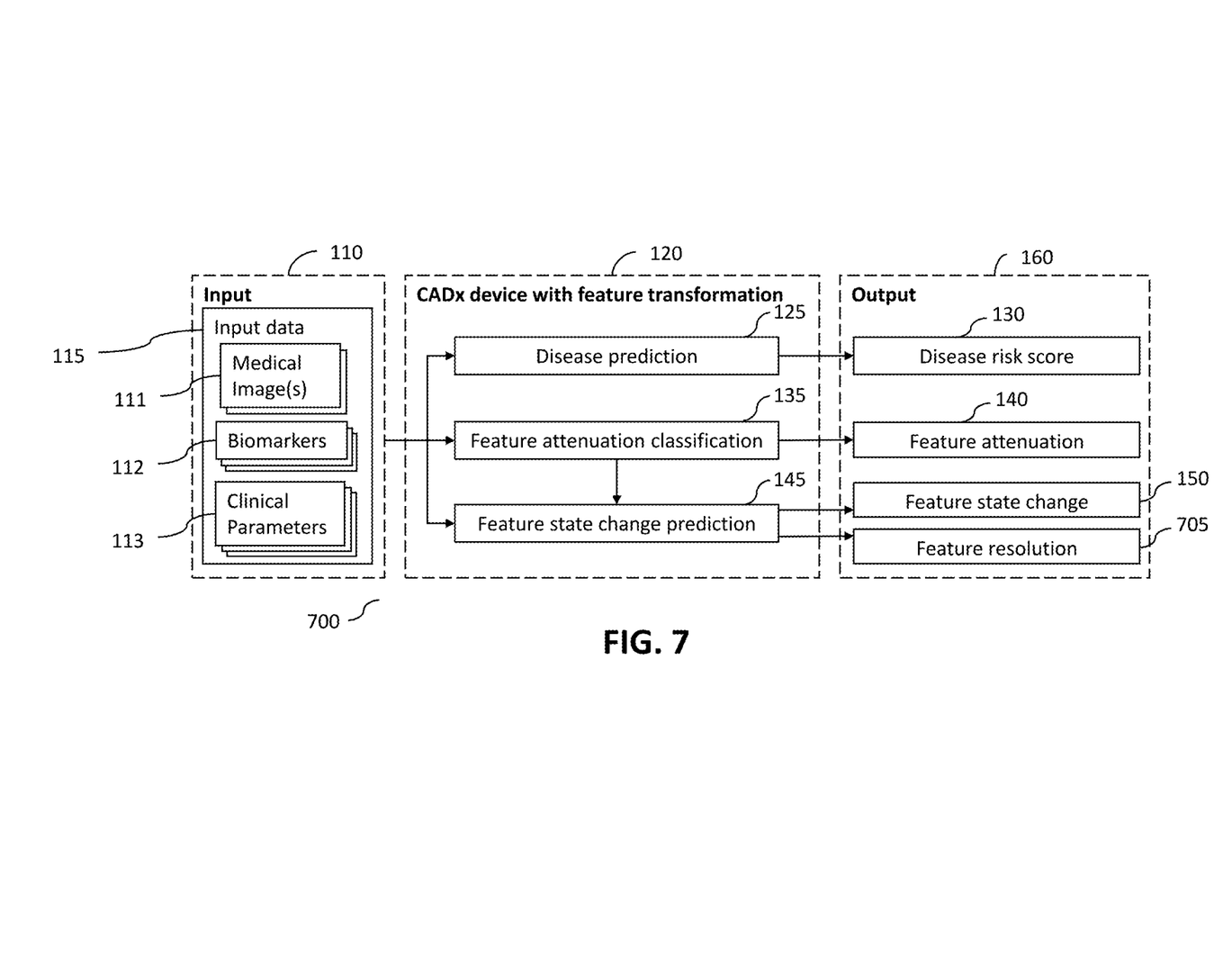
FIG. 7 shows an alternative embodiment of the CADx system of the invention.

In some example implementations of the CADx device with feature state change, the feature state change prediction circuit 145 provides an additional output called feature resolution 705, as shown in FIG. 7, preferably this is resolution of a particular feature in an image, where the resolution is a prediction of the time period in which the feature will be resolved and disappear from the image. Preferably the monitored feature is a pGGO nodule and the pGGO resolution 705 output aims to indicate to the user of the CADx device whether a pGGO nodule in the input data 115 is expected to resolve (e.g., disappear) within a particular time period. pGGO nodules which will be resolved will not require any further follow-up, thus this information can be used in certain clinical scenarios to inform on the clinical management for a particular patient with a pGGO.

Figure 8:
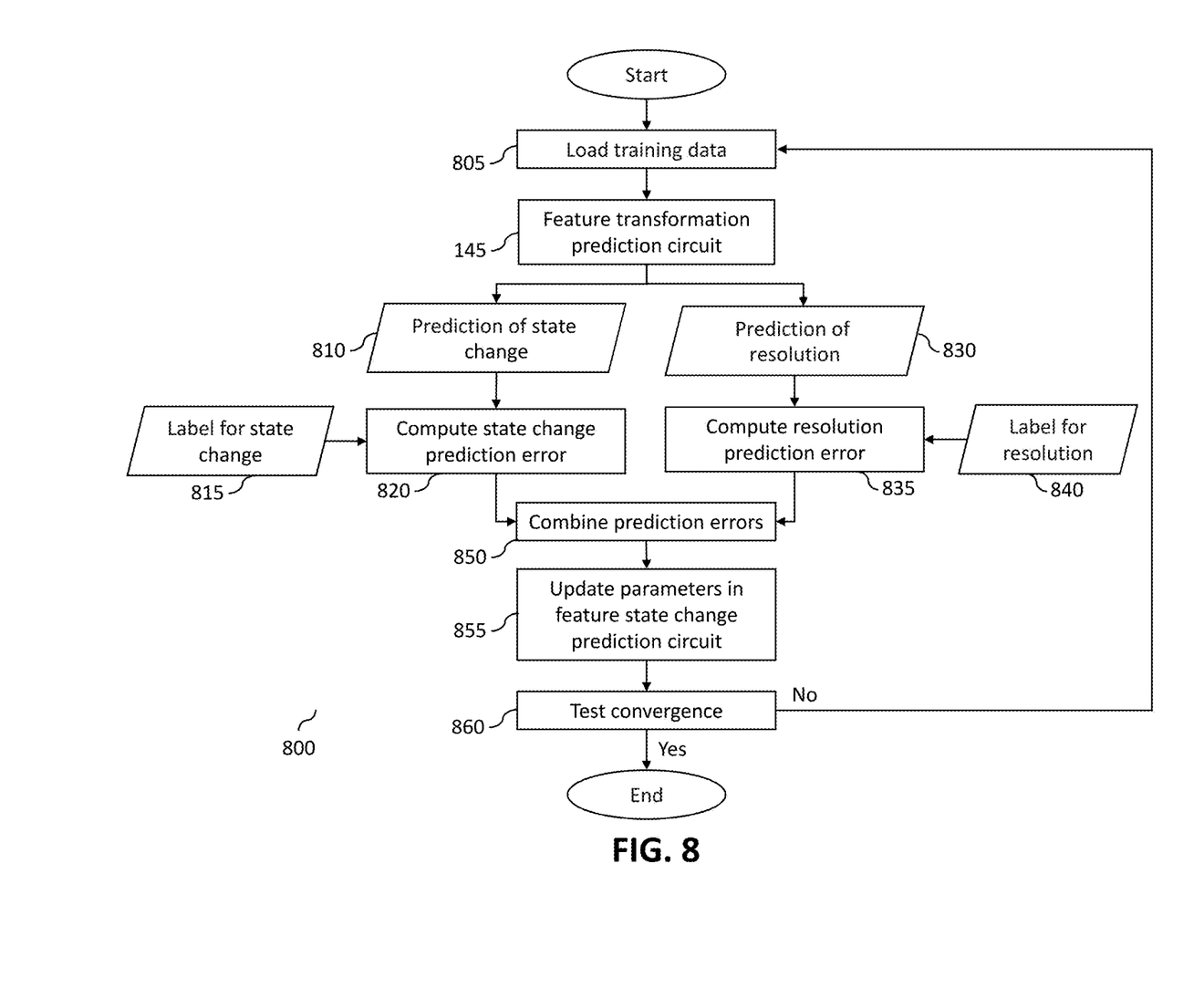
FIG. 8 shows a method for training a machine learning model for the CADx system as shown in FIG. 7.

In some example implementations of this invention, the prediction of the feature resolution, preferably resolution of a pGGO lung nodule is carried out by the feature state change prediction circuit 145 in parallel to the state change prediction; that is, the circuit 145 implements independent machine learning models for each of the two tasks. In other examples, the feature state change prediction circuit 145 implements a machine learning model that can perform both prediction tasks simultaneously. FIG. 8 shows the process 800 for training the feature state change prediction circuit 145 to perform the state change prediction 150 simultaneously to the feature resolution prediction 705. The process where these two tasks come from independent models can be trivially derived from 800 by a person skilled in the art.

In 800, the feature prediction task 810 refers to any of the embodiments of the feature state change prediction circuit 145 described in this invention. For example, those that may have obtained through training processes 500 and 600 described above.

Training the feature state change prediction circuit 145 to predict feature resolution, particularly pGGO resolution, requires a corpus of training data, as would be input to the CADx device 115 (e.g., CT images), but made up of features for which it can be determined whether they resolved within a specified timeframe denoted as $t_r$. For instance, follow-up studies exist for pGGO nodules. The output of this determination is denoted as the resolved-by-$t_r$ label, $1_r$. For example, pGGO nodules which have been followed-up for at least a time of $t_r$, can be assessed by an expert (e.g., radiologist) in order to determine whether the nodule resolved or persisted. In some cases, pGGO nodules may have been followed for less than $t_r$ because they resolved earlier, in which case they can be included as part of the training data as resolving pGGO nodules.

The training process 800 is an iterative one, where each iteration starts with the loading of the training data 805 which contains feature samples, preferably pGGO nodules, for which labels exist for both simultaneous prediction tasks: state change and resolution. Preferably the training data is a collection of images such as CT images. The loaded training data is given, either completely or partially, to the feature state change prediction circuit 145, which then computes separate predictions for both tasks (resolution and state change prediction). The prediction of the state change 810 is compared to the corresponding state change ground truth label 815 to compute a state change prediction error 820. Likewise, the prediction of feature resolution 830 is compared to the corresponding resolution label 840 to compute a resolution prediction error 835. The prediction errors for both tasks are then combined 850 into a single error signal which is used to update the parameters of the feature state change prediction circuit 145 in a way that simultaneously reduces the error signal of both prediction tasks. In some examples of this invention, the error signals of both tasks are combined by a mathematical addition operation. In other examples, the combination of error signals consists of the average of the error signal in each of the prediction tasks. Finally, the convergence of the training process is tested 860, for example, by comparing such as the combined error signal 850 against its value in previous iterations and determining the convergence of the process is the error signal has not changed. Once the process has converged, the training of the feature state change prediction circuit 145 is complete. Otherwise, a next iteration starts. The iterations are repeated until the test for convergence is satisfied.

Once trained, the feature state change prediction circuit 145 can predict, for a monitored feature such as a pGGO nodule in the input data 115, both a time period for the state change as well as a time period for the resolution.

In some example implementations of the feature state change prediction circuit 145, its structure is based on a deep neural network. In some examples, this deep neural network implements a multi-task model, where a subset of it is a classification model with two possible classes $c \in [0, 1]$ denoting whether the feature, such as a pGGO nodule resolves by $t_r$ or not. In example implementations where the resolution task occurs simultaneously with the state change prediction task, another subset of the deep neural network implements either a regression or a classification model, as per required by the different embodiments of the feature state change prediction circuit 145.

Typically, the raw output of the feature resolution classification deep neural network for a given unit of input data 115 consists of a scalar value $s_c$ for each of the two possible classes: resolution or persistence. In some example implementations, the scalar values $s_c$ are transformed into a probability distribution using a softmax function as in EQ. 3, resulting in $p_c$. Given that there are only two outcomes on this probability distribution, $p_c$ can be summarized with a single value $p_{t_r}$ which is indicative of the probability that the monitored feature nodule in the input data 115 will have resolved by the time $t_r$.

In some example implementations, the value $p_{t_r}$ is given to the output circuit of the CADx device 160 such that it can be presented to the user as the feature resolution 705. In other examples of this invention, the value $p_{t_r}$ is converted into a binary indicator of feature resolution by thresholding it in the following way $$\text{Resolution} = \begin{cases} \text{Yes, if } p_{t_r} \geq R_{th} \\ \text{No, if } p_{t_r} < R_{th} \end{cases} \quad (5)$$

Here, $R_{th}$ is a resolution threshold which is empirically set according to the clinical use-case of the CADx device. For example, if the feature resolution is used to decide whether to schedule a follow-up or not, $R_{th}$ should be set such that only cases that are very certain to resolve are flagged as such. That is, $R_{th}$ would be set such that the specificity of the prediction is very high.

CADx devices have been shown to aid in the diagnosis of a variety of conditions, including lung cancer. In the case of lung cancer, clinicians focus the diagnosis process on the cancer risk assessment of lung nodules, these being the typical presentation of lung cancer. State-of-the-art CADx devices for the diagnosis of lung cancer typically predict a cancer risk score which then helps clinicians plan the patient management. Nevertheless, pGGO nodules, a sub-class of lung nodules according to their attenuation in their radiological presentation, receive a different type of management than other types such as solid and semi-solid nodules. This invention enhances CADx devices for lung cancer diagnosis with the ability to provide information that is directly relevant to the management of pGGO nodules which cannot be achieved with standard lung cancer risk scores.

This invention can be applied in the context where a CADx device, powered by a machine learning model, is used to assess the risk of lung cancer from input medical data such as medical images.

Specific cases include:
- As part of decision support system used within a hospital or clinic that cares for patients with pulmonary nodules, where the managing clinicians would like to get an independent assessment of lung cancer risk for the nodule present in a patient based on medical data including medical images such as CT scans.
- As part of a platform to track and monitor patients with pulmonary nodules, where this invention is used to assess the risk of cancer of a patient in the platform's database to help the clinician chose the appropriate clinical pathway to follow.
- As part of a system that automatically parses large databases of CT scans of patients looking for nodules, e.g. within a large hospital system, which are then automatically assessed for risk of cancer using this invention in order to prompt the clinicians of high-risk cases that must be prioritized.

The present invention has been described with reference to the accompanying drawings. However, it will be appreciated that the present invention is not limited to the specific examples herein described and as illustrated in the accompanying drawings. Furthermore, because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The invention may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system. Therefore, some examples describe a non-transitory computer program product having executable program code stored therein for receiving at least one input medical image of a patient in which the patient's lungs are visible.

The computer program may be stored internally on a tangible and non-transitory computer readable storage medium or transmitted to the computer system via a computer readable transmission medium. All or some of the computer program may be provided on computer readable media permanently, removably or remotely coupled to an information processing system. The tangible and non-transitory computer readable media may include, for example and without limitation, any number of the following: magnetic storage media including disk and tape storage media; optical storage media such as compact disk media e.g., CD ROM, CD R, etc. and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing running program or portion of a program, current program values and state information, and the resources used by the operating system to manage the execution of the process. An operating system OS is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output I/O devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the scope of the invention as set forth in the appended claims and that the claims are not limited to the specific examples described above.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively 'associated' such that the desired functionality is achieved. Hence, any two components herein combined to achieve a particular functionality can be seen as 'associated with' each other such that the desired functionality is achieved, irrespective of architectures or intermediary components. Likewise, any two components so associated can also be viewed as being 'operably connected,' or 'operably coupled,' to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms 'a' or 'an,' as used herein, are defined as one or more than one. Also, the use of introductory phrases such as 'at least one' and 'one or more' in the claims should not be construed to imply that the introduction of another claim element by the indefinite articles 'a' or 'an' limits any particular claim containing such introduced claim element to inventions containing only one such element, even when the same claim includes the introductory phrases 'one or more' or 'at least one' and indefinite articles such as 'a' or 'an.' The same holds true for the use of definite articles. Unless stated otherwise, terms such as 'first' and 'second' are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

We claim:

1. A Computer Aided Detection (CADx) system for analysing medical images to monitor at least one feature on the image to predict at least one of a change of the state or maintenance of the current state of a monitored feature within a time frame comprising:
   an input circuit for receiving at least one medical input image;
   a feature state change circuit for analysing the received input image and predicting a state change comprising:
   a state change predictor to predict a state change of the monitored feature within the time frame; and
   an output circuit to output an indication of the change of state or maintenance of the current state of the monitored feature within the time frame based on the prediction of the state change predictor.

2. The Computer Aided Detection (CADx) system according to claim 1, wherein the feature state change circuit further comprises a feature attenuation classifier that activates the feature state change circuit when the at least one monitored state in a feature is detected.

3. The Computer Aided Detection (CADx) system according to claim 2, wherein the output circuit also provides an output of the current state of the monitored feature.

4. The Computer Aided Detection (CADx) system according to claim 1, where the feature state change circuit also predicts the resolution of the monitored feature.

5. The Computer Aided Detection (CADx) system according to claim 1, wherein the monitored feature is a lung nodule and the change of state of the monitored feature is from a pure ground glass opacity nodule to a solid or part solid nodule.

6. The Computer Aided Detection (CADx) system according to claim 1, wherein clinical parameters and biomarkers comprise at least one of: patient age, patient sex, results of blood tests, results of lung function tests.

7. The Computer Aided Detection (CADx) system according to claim 1, wherein the output circuit further outputs a disease risk score for the input medical image.

8. The Computer Aided Detection (CADx) system according to claim 1, wherein the input further comprises one or more biomarkers or clinical parameters for the patient.

9. The Computer Aided Detection (CADx) system according to claim 1, wherein the input medical image is one of: X-ray image, CT image, ultrasound image, MRI image, SPECT image or a PET image.

* * * * *